(12) United States Patent
Gruenbacher et al.

(10) Patent No.: US 6,508,602 B1
(45) Date of Patent: *Jan. 21, 2003

(54) SEMI-ENCLOSED APPLICATOR FOR DISTRIBUTING A SUBSTANCE ONTO A TARGET SURFACE

(75) Inventors: Dana Paul Gruenbacher, Fairfield, OH (US); James Herbert Davis, Middletown, OH (US); Kevin Joe Fields, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/451,536

(22) Filed: Dec. 1, 1999

Related U.S. Application Data

(63) Continuation-in-part of application No. 09/415,866, filed on Oct. 8, 1999.

(51) Int. Cl.[7] .......................... A47L 13/19; A61M 35/00
(52) U.S. Cl. .......................... 401/7; 15/104.94; 15/227; 401/133; 604/292
(58) Field of Search ................ 401/6, 7, 132–135; 15/104.94, 227; 604/292, 306

(56) References Cited

U.S. PATENT DOCUMENTS

| 2,279,100 | A | * | 4/1942 | Worth et al. ............... 401/7 |
| 2,790,982 | A | * | 5/1957 | Schneider .................. 401/7 |
| 3,053,385 | A | * | 9/1962 | Spees ..................... 401/132 X |
| 3,768,916 | A | | 10/1973 | Avery ..................... 401/132 |
| 3,870,150 | A | * | 3/1975 | Hummel ................... 15/227 X |
| 3,929,135 | A | | 12/1975 | Thompson ................. 128/287 |
| 4,081,256 | A | | 3/1978 | Donnelly .................... 62/4 |
| 4,324,246 | A | | 4/1982 | Mullane et al. ............. 128/287 |
| 4,342,314 | A | | 8/1982 | Radel et al. ............... 128/287 |
| 4,349,288 | A | * | 9/1982 | Bond ......................... 401/7 |
| 4,430,013 | A | | 2/1984 | Kaufman ................... 401/132 |
| 4,670,930 | A | | 6/1987 | Lu ........................... 15/118 |
| 4,878,775 | A | | 11/1989 | Norbury et al. ............ 401/132 |

(List continued on next page.)

FOREIGN PATENT DOCUMENTS

| DE | 3545926 A1 | 7/1987 | .......... D06N/7/00 |
| EP | 0 291 284 B1 | 11/1988 | .......... B05C/17/00 |
| EP | 0 291 284 A2 | 11/1988 | .......... B05C/17/00 |
| EP | 0 294 189 A2 | 12/1988 | .......... B65D/47/42 |
| EP | 638277 | * 2/1995 | .................. 15/227 |
| FR | 2 754 744 | 4/1998 | .......... B05D/1/28 |

Primary Examiner—Henry J. Recla
Assistant Examiner—Kathleen J. Prunner
(74) Attorney, Agent, or Firm—Peter D. Meyer; Larry L. Huston

(57) ABSTRACT

A semi-enclosed applicator is provided for distributing a substance onto a target surface. The applicator has a first side, a second side, and an internal cavity between the first and second sides. The applicator further includes at least one opening, such that the internal cavity is externally accessible. The applicator further comprises: (a) a substantially non-absorbent material on one of the first and second sides; (b) a substantially absorbent material on the other of the first and second sides; and (c) a substantially fluid-impervious barrier layer within the internal cavity adjacent the nonabsorbent layer. A semi-enclosed applicator is also provided for distributing a substance onto a target surface. This applicator has a first side, a second side, and an internal cavity between the first and second sides. The applicator further includes at least one opening, such that the internal cavity is externally accessible, and the applicator further comprises: (a) a substantially fluid-impervious barrier layer within the internal cavity adjacent one of the sides; and (b) a rupturable fluid-containing reservoir located between the barrier layer and the side.

39 Claims, 4 Drawing Sheets

U.S. PATENT DOCUMENTS

| | | | |
|---|---|---|---|
| 4,891,258 A | * | 1/1990 | Fahrenkrug .................. 428/138 |
| 4,902,283 A | | 2/1990 | Rojko et al. ................. 604/290 |
| 4,928,322 A | | 5/1990 | Bradfield ........................ 2/169 |
| 4,953,250 A | | 9/1990 | Brown .................... 15/104.94 |
| 4,959,881 A | | 10/1990 | Murray ......................... 15/227 |
| 5,090,832 A | | 2/1992 | Rivera et al. ................ 401/132 |
| 5,454,207 A | | 10/1995 | Storandt ....................... 53/410 |
| 5,473,789 A | | 12/1995 | Oster ...................... 15/104.94 |
| 5,616,201 A | | 4/1997 | Finch et al. ................ 156/73.1 |
| 5,658,084 A | | 8/1997 | Wirt ............................ 401/132 |
| 5,738,212 A | | 4/1998 | Pollard et al. .............. 206/362 |
| 5,806,099 A | | 9/1998 | Grinberg ........................ 2/158 |
| 5,829,089 A | | 11/1998 | Steadman ..................... 15/227 |
| 5,867,829 A | | 2/1999 | Hegoas et al. ................. 2/159 |
| 6,305,044 B1 | | 10/2001 | James et al. |
| 2001/0036803 A1 | | 11/2001 | Fisher |

* cited by examiner

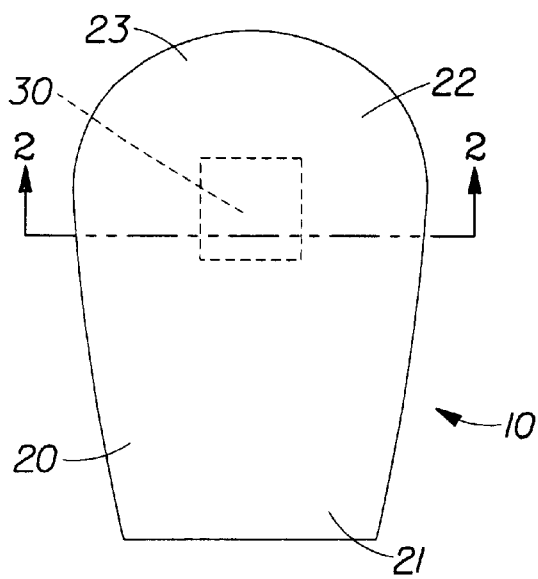
Fig. 1
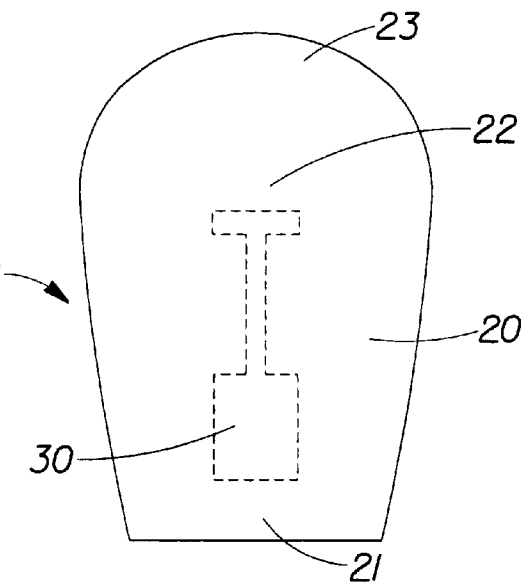
Fig. 3
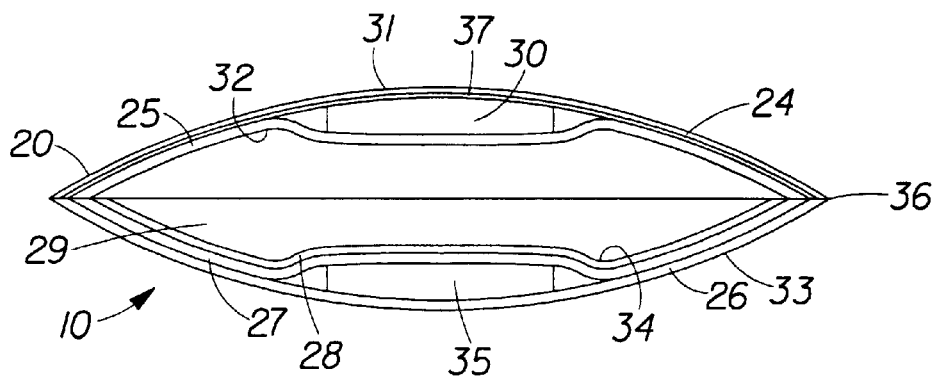
Fig. 2
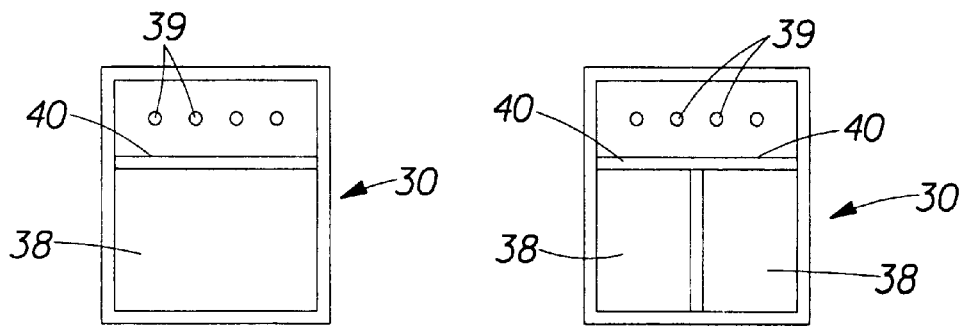
Fig. 4
Fig. 5

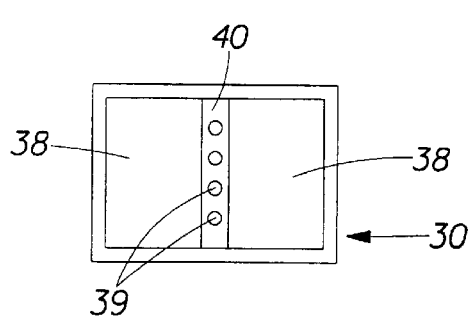
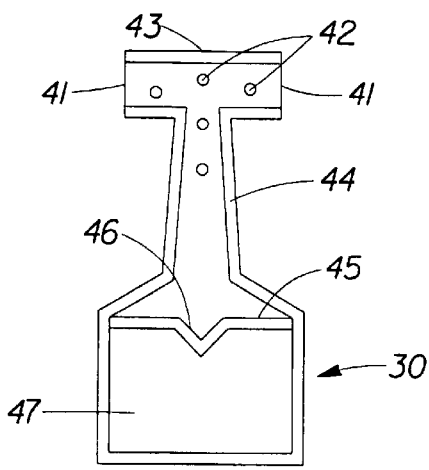
Fig. 6
Fig. 7
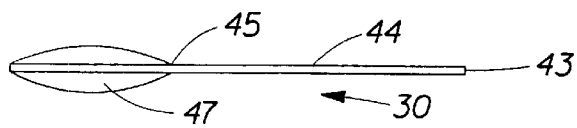
Fig. 8
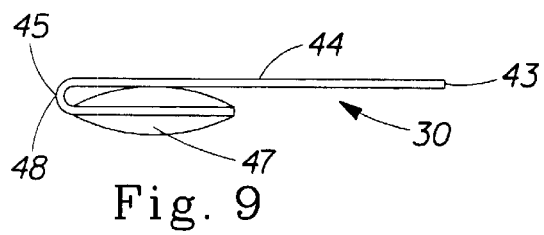
Fig. 9
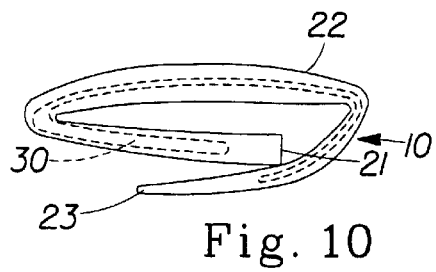
Fig. 10
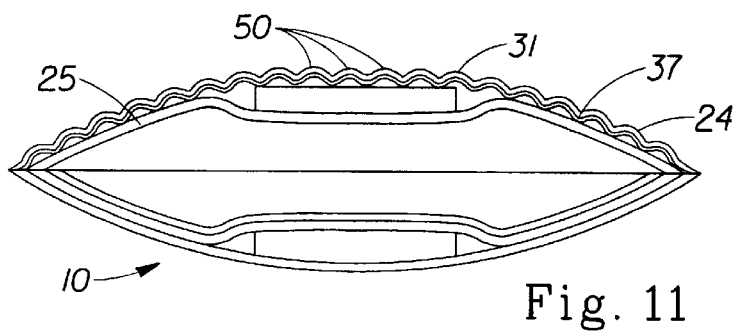
Fig. 11
Fig. 12
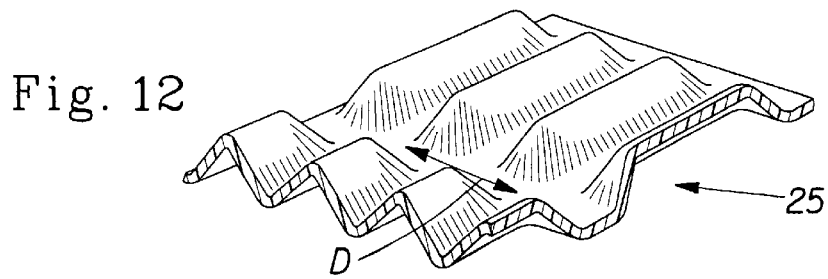

SEMI-ENCLOSED APPLICATOR FOR DISTRIBUTING A SUBSTANCE ONTO A TARGET SURFACE

This is a Continuation-in-part of Application Ser. No. 09/415,866, filed Oct. 8, 1999.

FIELD OF THE INVENTION

The present invention relates to a semi-enclosed applicator useful for distributing substances onto target surfaces. The present invention also relates to such an applicator which also contains a substance for application to the surface of a target object. More particularly, the present invention relates to such applicators wherein the substance may be released from the applicator material and distributed upon the surface of the target object, then removed from the surface and absorbed by the applicator.

BACKGROUND OF THE INVENTION

In the art of dispensing, articles have been developed which are coated or impregnated with useful substances intended to be utilized when the article is contacted with a target surface. While there are advantages with having the substance present on or near the surface of such articles, there is often the drawback that the useful substance is unprotected and is subject to inadvertent contact before intended use. Inadvertent contact may lead to contamination of the substance, loss of the substance onto surfaces other than the desired target surface, and/or contamination of such other surfaces with the substance. Moreover, the use of such articles to manually apply a substance to a surface of an object frequently results in exposure of a user's hands to the substance. At the very least such a scenario results in a waste of product and is undesirable from an aesthetic standpoint and, at worst, results in excessive exposure of the user to potentially harmful, toxic, or otherwise undesirable substances.

Other common approaches involve dispensing a substance such as a cleaner or protectant from a bottle or other closed vessel onto the target surface, then utilizing a sponge, towel, brush, or other implement to distribute the product on the surface and, if desired, absorb any excess product, potentially with another implement or substrate. Such practices are commonplace with surfaces such as glass, countertops, and other kitchen and bathroom surfaces. While such practices are widely accepted, they often result in inefficient use of product and/or contact with the substances involved. Moreover, utilizing such an implement typically only provides one type of material surface for use in contacting the substance and the target surface. Applying the substance to the applicator from a vessel at the point of use likewise often results in inefficient use of product and/or contact with the substances involved.

Accordingly, it would be desirable to provide an applicator for applying a substance to a target surface which permits greater control by the user during the application process.

It would also be desirable to provide such an applicator which permits the user to apply a substance to a target surface with reduced messiness and waste of the substance.

It would further be desirable to provide such an applicator which provides multiple surfaces of diverse materials and/or multiple substances for use in multiple tasks.

SUMMARY OF THE INVENTION

The present invention provides a semi-enclosed applicator for distributing a substance onto a target surface and a method for making such an applicator. The applicator has a first side, a second side, and an internal cavity between the first and second sides. The applicator further includes at least one opening, such that the internal cavity is externally accessible, and, in a preferred embodiment, the applicator further comprises: (a) a substantially non-absorbent fibrous material on one of the first and second sides; (b) a substantially absorbent fibrous material on the other of the first and second sides; and (c) a substantially fluid-impervious barrier layer within the internal cavity adjacent the non-absorbent material.

The present invention also provides a semi-enclosed applicator for distributing a substance onto a target surface, the applicator having a first side, a second side, and an internal cavity between the first and second sides. The applicator further includes at least one opening, such that the internal cavity is externally accessible, and the applicator further comprises: (a) a substantially fluid-impervious barrier layer within the internal cavity adjacent one of the sides; and (b) a rupturable fluid-containing reservoir located between the barrier layer and the side.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements, reference numerals with the same final two digits identify corresponding elements, and wherein:

FIG. 1 is a plan view of a preferred embodiment of a semi-enclosed applicator in accordance with the present invention, in the form of a mitt;

FIG. 2 is a cross-sectional view of the mitt of FIG. 1 taken along line 2—2;

FIG. 3 is another embodiment of a semi-enclosed applicator in accordance with the present invention, also in the form of a mitt;

FIG. 4 is a plan view of one embodiment of a rupturable reservoir suitable for use in accordance with the present invention;

FIG. 5 is a plan view of another embodiment of a rupturable reservoir suitable for use in accordance with the present invention;

FIG. 6 is a plan view of a further embodiment of a rupturable reservoir suitable for use in accordance with the present invention;

FIG. 7 is a plan view of a further embodiment of a rupturable reservoir suitable for use in accordance with the present invention;

FIG. 8 is an elevational view of the rupturable reservoir of FIG. 7;

FIG. 9 is an elevational view of the rupturable reservoir of FIG. 8 folded in the vicinity of the rupturable seal;

FIG. 10 is an elevational view of an applicator similar to that of FIG. 3 which is folded in the vicinity of the rupturable seal of the rupturable reservoir;

FIG. 11 is a cross-sectional view of an applicator similar to that of FIGS. 1 and 2, but illustrating the use of rugosities on at least one surface;

FIG. 12 is a partial perspective view of one material useful in forming the rugosities of FIG. 11;

DETAILED DESCRIPTION OF THE INVENTION

Figure 13:
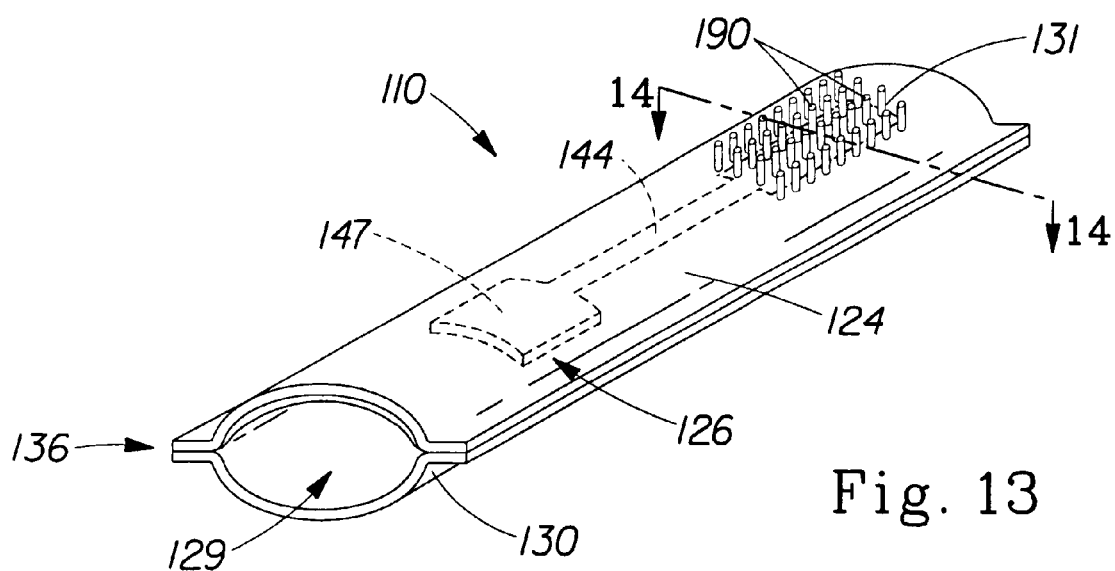
FIG. 13 is a perspective view of an exemplary finger mitt applicator made in accordance with the present invention.

As used herein, the term "hand article", refers to a covering for the hand or portion of the hand such as a finger or thumb. The term "disposable" is used herein to describe hand articles which are not intended to be restored or reused (i.e., they are intended to be discarded after a single use or a limited number of uses, and preferably, to be recycled, composted or otherwise disposed of in an environmentally compatible manner). As used herein the term "glove" refers to a covering for the hand having separate sections for each finger. As used herein, the term "mitt" refers to a covering for the hand having an enclosure that leaves the fingers unseparated and that may include space for the thumb in the main enclosure, or provide space for the thumb in a separate enclosure for the thumb, or may not include a thumb enclosure at all. This term is also applicable to an apparatus which covers only one or more digits of a user, such as in the case of a "finger mitt" as described below. While the terms "glove" and "mitt" have been defined with respect to the human hand, similar structures could be utilized to cover or enclose other elements of human anatomy, such as foot coverings, or other items for which coverings of a particular shape are preferred. As used herein the term "extension force" refers to forces applied by hand movements to a surface to extend and/or bend that surface linearly and/or curvilinearly.

The term "semi-enclosed applicator" is intended to refer to an applicator device having at least one externally-accessible internal cavity for receiving a portion of human anatomy such as a hand or finger so that the applicator device may be used as an implement. A glove, mitt or finger mitt would be an example of such a semi-enclosed applicator in the context of the present invention.

Applicator Construction and Operation:

A representative embodiment of a semi-enclosed applicator of the present invention in the form of a hand article is the disposable mitt 10 shown in FIG. 1. FIG. 1 is a plan view of the mitt 10 of the present invention in its flat-out state illustrating the body portion 20, cuff portion 21, central portion 22, distal portion 23, and reservoir 30. In general terms, the mitt 10 has an internal cavity which is accessible through an opening in the cuff portion and extends inwardly to the distal portion which is closed.

FIG. 2 shows more specifically the construction details of the mitt 10 the mitt 10 has a front outer surface 31, a front inner surface 32, a back outer surface 33, and a back inner surface 34. The front and back inner surfaces define a hollow interior 29 into which a hand may be inserted through an opening in the cuff portion 21. The mitt 10 includes a front panel 24, which defines the front outer surface 31, and a back panel 26 which defines the back outer surface 33. The front and back panels are connected along their periphery to form a seam 36. For a typical hand article, the back panel is adjacent to the back of a user's hand during use and the front panel is adjacent to the palm of a user's hand during use.

In accordance with the present invention, the front panel 24 comprises a porous, preferably nonwoven, material through which the liquid within the reservoir 30 can be dispensed. In order to provide for residence time of the liquid upon the target surface, the material utilized for the front panel 24 is preferably substantially non-absorbent, and preferably substantially hydrophobic when utilized with water-based liquids. One material of current interest for such applications is a polypropylene nonwoven fibrous material. Another applicable material would include an open or closed cell polyethylene foam, such as available from Sentinel Products Corp. of Hyannis, Mass. Suitable materials for use as a front panel 24 also provide sufficient strength and texture characteristics so as to provide a scrubbing action upon the target surface and to maintain web integrity when exposed to the liquid. Additional, or alternative, fibers such as PET fibers can be utilized for additional strength and scrubbing capability.

In view of the fact that polypropylene nonwovens, and many other suitable materials for front panel 24, are highly porous and rapidly penetrated by liquids, the mitts of the present invention preferably but optionally include a tissue paper layer 37 between the reservoir 30 and the front panel 24. A suitable material is a single ply of disposable kitchen paper towel such as BOUNTY®, a product of The Procter & Gamble Company. Such a material is capable of wicking the liquid of interest and distributing the liquid beyond the dimensions of the reservoir and supplying liquid to a larger surface area of the outer layer (front panel 24). This wicking layer may also be desirable to help control fluids of low viscosity as they are distributed to the front panel for dispensing.

In order to protect the hand of the user from contact with the liquid during the dispensing and dispersing operation, the mitts of the present invention include a fluid impervious barrier layer 25, the interior of which defines the front inner surface 32 that faces the wearer's hand during use. Suitable barrier materials include polyethylene films, which may be rendered extensible by methods to be described hereafter. Materials which are embossed, whether or not rendered extensible, provide improved tactile properties and greater control over the applicator in terms of contact and coefficient of friction with the hand.

The fluid reservoir 30 may be of any suitable size, configuration, and composition for the intended liquid to be dispensed and dispersed. One aspect of the reservoir 30 which is believed to be important to the overall functionality of the mitt 10 is the ability of a sealed, fully-enclosed reservoir to rupture or otherwise dispense the liquid contained therein when "activated" by the user and yet resist premature dispensing during manufacture, packaging, and shipment. In alternate embodiments, the reservoir may be located at least partially outside of the applicator 10. For example, chamber 47 of reservoir 30 of FIG. 7 might extend outwardly from an applicator for improved visual and manual access, as desired. The ability of the reservoir to survive intact until the point of use preserves the quality and quantity of the liquid until the time of use. As will be understood, external accessibility to a reservoir might also facilitate the provision of crimping devices, folding of a reservoir or other protection of the reservoir against premature dispensing, as will be discussed further below.

The rupturable reservoir is designed to burst or rupture to release the fluid contained therein at a comparatively low force when desired by the consumer. This may be accomplished by having a sealed pouch with permanent seals and also seals that are "frangible", i.e., rupturable. When the pouch is squeezed, the frangible seal will yield or fail first since it has a lower peel force to break the seal apart than the permanent seals. The frangible seal will ideally rupture with 1–3 lbs of force when applied by the consumer. The location of rupture can be enhanced by adding stress concentrators in the seal geometry that will localize forces at a particular location. These stress concentrators can be shaped like a V, a notch, a half circle or a variety of other shapes depending upon the desired burst level. These stress concentrators will help control the force required to burst the pouch as well as the location of where the seal will rupture. Such stress concentrators thereby focus or concentrate external pressure or mechanical forces imposed on the reservoir and its contents. For example, pressurizing a pouch having a V-notch seal such as shown in FIG. 7 will localize forces first at the apex of the V, causing that region to rupture first. Such an arrangement can help reduce potential variability in rupture or dispensing forces and the location where the rupture occurs. It will be understood that seal angles and geometries of such seal can be used to tailor dispensing forces for particular applications.

In the embodiment of FIG. 1, the reservoir 30 is positioned in the central region 22 of the mitt 10. In this location, the reservoir 30 can be subjected to sufficient force to rupture the reservoir and dispense the liquid by making a fist with the user's hand, by applying force with the opposite hand, or by pressing the palm against the target surface. This location of the reservoir in the applicator is convenient for applications where it is desired for the product to be dispensed all at once or while rubbing a surface. It may also be desired to have the reservoir located in a portion of the applicator which is spaced or remote from where the forces applied during cleaning or rubbing does not cause premature dispensing or dosing. FIG. 3 depicts an alternative embodiment of a mitt 10 wherein the reservoir 30 is positioned closer to the cuff region 21. In this location, the reservoir is not located in the region of the mitt which would typically encounter forces in use (the application or pressure region), and would require activation by specifically applying force to the cuff region. Such an embodiment may be particularly advantageous where progressive dispensing of discrete quantities of fluid is desired rather than an "all at once" dispensing upon application of an initial force.

The use of a reservoir to contain a fluid is needed to allow the applicator to become wet on the desired side only when wanted by the person using the applicator. In some cases a person would like to store a single applicator in a remote site like for instance the glove box in the car or in a separate drawer in a bathroom. The hermetically sealed reservoir(s) in the applicator preferably use sufficient barrier materials to allow these individual applicators to have multi-year shelf life even when stored as individual units. Separately, the reservoirs can be placed on one or both sides of the applicator or in multiples on the same side. This allows one side to be kept dry or to have different substances on the different sides. In contrast, pre-moistened wet wipes that have been individually wrapped are traditionally placed in a foil pouch. This foil pouch material is expensive and more of it is needed to enclose the entire wipe to prevent moisture loss (with the individually enclosed reservoir, foil film is only needed to enclose the liquid or substance). This approach of putting the entire pre-moistened applicator (wipe) in a foil pouch also makes it difficult for the wipe to have a dry surface or from having surfaces with two different substances since cross-contamination is likely to occur.

The reservoir preferably uses a laminate film that contains either metallized PET, aluminum foil, $SiO_2$ or some other high barrier material that will provide adequate moisture and oxygen barrier to allow the product to have a 2–3 year shelf life. Smaller reservoirs with small amounts of a fluid require even a higher barrier since the surface area to volume of fluid is significantly higher resulting in higher levels of moisture loss due to transport and diffusion.

The reservoirs can be made rupturable or "frangible" by a number of different techniques. One preferred technique is to make a pouch on a vertical or horizontal form/fill/seal machine that has the ability to make different seals on the pouch at different temperatures, pressures or seal times. This allows one side of a pouch to have different sealing conditions which in turn can allow one side to have a weaker seal strength. A suitable sealant material for this type of "frangible" seal would be Surlyn made by Dupont or a blend of Polybutylene with Ethylene Vinyl Acetate or Metallocene Polyethylenes, and/or Polyethylene. Sealant layers made with either of these resins or blends will result in a sealant layer that will have significantly different seal strengths depending upon the seal temperature. The blend provides a "contaminant" to the base polymer material which allows the resulting seal to be selectively frangible under certain sealing conditions. For example, at 200° F. the sealant layer will deliver a seal force of 200–400 grams/linear inch of seal width and at 300° F. the seal force will deliver a seal force closer to 3000 grams/linear inch of seal width. This variation in seal strength allows a pouch to be "welded" shut on 3 sides and one side easily burstable just by adjusting the seal temperature used when making the pouch seals. A preferable film structure for this type of frangible reservoir would be Surlyn sealant/tie layer/metallized PET.

Other techniques for making the consumer activated rupturable reservoirs would include delaminating seals, embossed or scored weak regions in the laminate that would rupture, and small thermoformed cells with thin regions that rupture when squeezed (similar to bubble wrap).

Applicators such as mitts may, as described herein, be designed to deliver substances to one or both surfaces, or be utilized independently with substances applied via other sources to accomplish dispersion of the substance and, if desired, removal of the substance from the surface by absorption. Applicators, however, may be similarly designed to direct substances toward the opposite surfaces of the mitt after eversion, for example, if the mitt is used for one function, then turned inside out and then activated again to deliver fresh substance from the former internal surface.

One approach to designing such an applicator, for example, as a baby cleaning mitt, would involve one of the rupturable reservoir being situated to wet a substrate on the initially inside of the mitt. With this example the outside of the mitt becomes wetted with a cleaning solution to clean the baby. One side of the mitt can be kept dry allowing the baby's skin to be patted dry. The mitt can then be everted and sealed shut with a layer of pressure sensitive adhesive that can be applied to the outer cuff region of the mitt such when the mitt is everted the cuff can be pressed shut and held tightly closed by the adhesive. Closing the everted mitt reduces odor and chance for loose bowel movement from falling off the mitt. The everted mitt now also exposes two new surfaces where one or both surfaces can have a rupturable reservoir for applying an additional substance to the baby's skin. A preferred substance would be a lotion that moisturizes and prevents diaper rash. In this case the everted and sealed shut mitt has become a two-sided wipe with the ability to apply additional substances if needed. The rupturable reservoirs for the inside surfaces would need to either be located in a region that prevent pre-mature bursting or have a higher burst force level so that they don't burst when the person is initially performing the cleaning task.

FIG. 4 illustrates one suitable configuration for a rupturable reservoir 30 suitable for use with applicators according to the present invention, such as the applicator of FIG. 1. In the embodiment of FIG. 4, the reservoir 30 includes a fluid-containing chamber 38, a frangible seal 40, and at least one dispensing aperture 39. The embodiment of FIG. 4 may be made by peripherally joining two similarly-sized and shaped pieces of fluid-impervious material with substantially permanent seals, forming the dispensing apertures in one portion of at least one of the pieces of material, introducing the liquid through one of the apertures, and then forming a frangible seal of limited strength to separate the chamber 38 from the apertures 39. Other forming techniques, such as folding a single piece of material double upon itself, or rolling a piece of material to form a sleeve, may also be utilized.

FIG. 5 depicts another embodiment of a reservoir 30 which is functionally similar to that of FIG. 4, but including a plurality of chambers 38 for containing liquid. Respective chambers 38 may include fluid of the same, similar, or diverse compositions, and may be designed to be ruptured sequentially or simultaneously depending on how pressure or squeezing is applied by the user. FIG. 6 is a further embodiment having a plurality of chambers 38, but wherein the chambers are themselves separated from one another by the rupturable seal 40. In such an embodiment, the chambers would typically be released concurrently, such as to mix the fluids from respective compartments at the time of dispensing.

The mitts of the present invention may have a burstable reservoir that has multiple chambers for mixing incompatible fluids. This would allow the ability to deliver superior cleaning performance as an example at an affordable cost. For instance, a chamber could have a bleach formula suitable for killing mildew, and germs and the other chamber could contain surfactants and cleaning solutions suitable for removing dirt and soap scum. The ideal formula's for these two different tasks are incompatible for a long period of time (like on a store shelf), but can be mixed right before use (like in the mitt) to deliver superior cleaning performance of nearly any type of bathroom stain. The same could be done for a variety of other uses like a disposable finger toothbrush that dispenses baking soda and peroxide on a "finger" mitt that allows these two products to be mixed to deliver superior teeth cleaning in a disposable package for away from home occurrences. The back side of the mitt could have a post-treatment for whitening the teeth.

More advanced fluid distribution functionality may be designed into the rupturable reservoir and/or to the applicator. The bursting pouch may also have an integral distribution head (such as illustrated as channel 44 of FIG. 7) that allows the product to be dispensed and dosed to different portions of the mitt. This distribution head is ideally an extension of the pouch material that has been sealed in a way to form channels for the fluid to flow to another region. The distribution head may have holes in the sides for the fluid to exit or may have several seals that force the fluid to change direction minimizing the velocity of the fluid exiting and thus reducing uncontrolled spraying of the fluid out of the mitt. Other arrangements, such as the inclusion of baffling structure to divert or control the fluid might be desirable as well, such as where fluids of low viscosity are dispensed.

FIG. 7 is one example of a more complex reservoir design. The reservoir 30 of FIG. 7 includes a plurality of outlet ducts 41, a plurality of distribution apertures 42, and an elongated channel 44 which separates the chamber 47 from the distal end 43 of the assembly. Fluid flow between the chamber 47 and the channel 44 is controlled by the frangible or rupturable seal 45, which illustrates the use of a stress-concentration notch 46. The channel 44 may be of a material and configuration such that it is "self-sealing" and collapses shut to restrict, if not preclude, fluid flow except when the chamber is substantially pressurized. For example, a channel may be formed by making two substantially parallel seals along facing layers of a pouch, where the space between these seals becomes a channel for fluid to move from the reservoir to the distribution aperture(s). The channel will naturally lay flat (and thereby closed) due to the seals, but will become almost tubular when the reservoir is pressurized and filled with fluid traveling through the channel. Upon release of the pressure, the channel will tend to naturally return to its flat state, causing a sealing effect to prevent further product delivery. Such a structure would thus provide the opportunity for dosing or progressive fluid dispensing. The outlet ducts and/or the apertures may be used as desired, with one or the other being employed or both in combination. Other approaches to provide dosing capability (i.e., multiple discrete dispensing cycles) include providing multiple reservoirs on either or both sides of the applicator.

It is desired for the pouch to rupture at 1–3 lbs when the consumer is ready to use the mitt but it is desired the pouch survive forces of 10–40 lbs when the mitt is in distribution to the store or handled in the box on the store shelf. This can be accomplished by folding the pouch on the frangible seal such that there is a mechanical advantage that occurs preventing the pouch from busting and generally protect the pouch from undesired rupture and premature fluid dispensing. This technique has been shown to effectively raise the bursting force to a level of 30–40 lbs. This can be accomplished by folding the mitt into a compact unit which also aids in packaging and shelf display. The mitt is ideally tri-folded such that the frangible seal is protected and the distribution head is also folded to provide an extra level of protection on the seal.

FIG. 8 is an elevational view of the reservoir of FIG. 7. FIG. 9 illustrates the use of folding techniques to protect a frangible seal from premature rupture. FIG. 9 illustrates a reservoir 30 consistent with that of FIGS. 7 and 8 which has been folded at location 48 which is adjacent the rupturable seal 45. Folding the reservoir in effect crimps, or pinches off, the fluid pathway and is capable of withstanding significantly more internal pressure without leakage than would normally be desired for the frangible or rupturable seal relied upon for dispensing functionality.

FIG. 10 illustrates the tri-folding of an applicator 10 to isolate the fluid-containing reservoir 30. As shown in FIG. 10, the additional fold in the vicinity of the distal end of the reservoir 30 may serve to provide additional security against premature dispensing by isolating the fluid outlets from the remainder of the reservoir. Bi-fold, tri-fold, z-fold, or any suitable folding mechanism may be utilized to provide not only a more compact applicator, such as when a plurality of applicators are folded, stacked, and then placed within a carton, sleeve, or outer wrapper, but also provide desirable functionality in terms of providing enhanced resistance to premature activation via a higher dispensing threshold prior to the point of use.

Another means of reducing pre-mature bursting is the use of a secondary crimping device that "clamps" the frangible seal and prevents pre-mature bursting until the crimping device is removed. This crimping device could be a low cost injection molded part such as a flexible clip or paper clip-like structure. The crimping device should have enough biasing force to keep the pouch in a generally flat condition adjacent the frangible seal or any region where protection from bursting is needed. A third approach is to have a pouch that is only partially filled but when folded has the right fill volume that allows the pouch to be burst when squeezing. When flat, the pouch can be squeezed and not burst since the fluid can flow to other portions of the pouch before the two sides of the pouch touch each other and bottom-out when squeezing.

After the liquid product has been dispensed and dispersed onto the target surface, it is typically desirable to absorb and remove excess liquid from the target surface. Accordingly, the back panel 26 of the mitt 10 is made from a material which is highly absorbent for the liquid of interest. For aqueous liquids, a single layer of 2-ply disposable kitchen paper towel such as BOUNTY RINSE AND REUSE®, a product of The Procter & Gamble Company, has been found suitable for use. The back panel preferably has sufficient absorbent capacity to absorb the quantity of liquid dispensed from the reservoir without oversaturation or substantial loss of web integrity. Due to evaporation, absorption into the target surface, and other effects, however, the back panel often is not expected to absorb the entire quantity of delivered fluid. Additional additives such as wet strength agents may be employed if desired. Another suitable material for higher wet strength applications may be a wet wipe substrate such as those available from Dexter Nonwovens comprising cellulose, rayon, and PET fibers for enhanced strength.

To protect the wearer's hand from contact with liquids absorbed by the back panel 26, it may be desirable for some applications to include an optional additional fluid impervious barrier layer 27, the interior of which defines the back inner surface 34 that faces the wearer's hand during use. Suitable barrier materials include polyethylene films, which may be rendered extensible by methods to be described hereafter.

Particularly when a second barrier layer 27 is employed, it may be desirable for some applications to include an optional secondary fluid reservoir 35 to deliver a second, possibly of diverse composition, liquid to the target surface. One example of such a scenario would be the use of water or a neutralizing agent in the secondary reservoir after the liquid in the primary reservoir has been utilized.

The interior surfaces of the mitt, particularly the back inner surface 34, may be optionally provided with friction-enhancing elements or coatings 28 to prevent slippage between the wearer's hand and the back inner surface, which could lead to rolling or rotating of the mitt upon the hand when the frictional forces between the back panel and the increasingly dry target surface escalate. Suitable elements include strips or beads of rubber, thermoplastic elastomers (e.g., KRATON®), or other suitable materials which can be applied by spray or slot coating, by gravure printing, or by adhesively or otherwise securing separate pre-formed elements.

In use, a wearer of the mitt 10 inserts a hand into the hollow interior through the provided opening at the cuff region 21 wherein the back panel contacts the back of the wearer's hand and the front panel contacts the wearer's palm. As the construction of the mitt 10 is more generic than a glove with defined anatomically-conforming geometry, the mitt may be used for either hand and/or may be appropriately sized to fit the foot of a wearer or any other bodily extremity.

If desired, at the end of its use, the mitt can be everted by making a fist with the mitt-hand, pulling the structure over the fist from the cuff region 21 of the mitt 10. Thus the layers are transposed, and the inner surface of the front panel and the inner surface of the back panel become the outer surfaces of the now waste article. More simply stated, the mitt is turned inside out after its use and then thrown away. That is, the wearer makes a fist, and with his or her other hand, grasps a point on the cuff region and carefully pulls the fisted hand toward the open mouth of the mitt, until the entire end of the mitt is pulled through the cuff.

In a preferred embodiment, the mitt 10 is a differentially extensible hand article wherein at least a portion of the glove extends and/or contracts about a wearer's hand and/or wrist without the use of traditional elastic such as natural or synthetic rubber. By the term "differentially extensible" or "differential extensibility" it is meant herein to describe that quality of extensibility wherein portions of the glove extend or contract independently of other portions in response to varying hand sizes and motions. Preferably, this differential extensibility allows a range of hand sizes to fit comfortably within the mitt. The mitt 10 may be provided with differential extensibility by utilizing a structural elastic-like film web such as those described in commonly-assigned U.S. Pat. Nos. 5,518,801, issued to Chappell, et al. on May 21, 1996, and U.S. Pat. No. 5,650,214, issued Jul. 22, 1997 in the names of Anderson et al., and commonly-assigned, co-pending U.S. patent application Ser. No. 08/635,220, filed Apr. 17, 1996 in the names of Davis et al., entitled "Fitted Glove", the disclosures of each of which are hereby incorporated herein by reference. Alternatively, differential extensibility to fit varying sized hands comfortably can be accomplished by various elastic-like materials, composite materials that produce elastic-like characteristics and/or processes to make a material(s) more elastic-like. As used herein, the term "elastic-like" describes the behavior of web materials such as web materials which, when subjected to an applied elongation, extend in the direction of applied elongation. Also, when the applied elongation is released the web materials return, to a substantial degree, to their untensioned condition. The term "web" as used herein refers to a sheet-like material comprising a single layer of material or a laminate of two or more layers.

The use of differentially extensible materials and suitable manufacturing processes, such as those described below, may be utilized to create a corrugation or pleating of at least one surface of the applicator, also characterized as a plurality of "rugosities". FIG. 11 illustrates a cross-sectional view of an applicator similar to that of FIGS. 1 and 2, but depicting the use of rugosities on an applicator surface. The applicator 10 of FIG. 11 is structurally similar to the cross-sectional view of FIG. 2, and therefore many of the reference numerals are omitted in the interest of clarity. However, as shown in FIG. 11, the fluid-impervious barrier layer 25 is provided with differentially extensible properties, preferably in accordance with the aforementioned commonly-assigned U.S. patents to Chappell, et al., and Anderson, et al., and therefore provides a plurality of rugosities 50 to the front outer surface 31 via the pleating or corrugation of the tissue layer 37 and front panel 24. Such rugosities would be, in the embodiment of FIG. 11, parallel pleats or corrugations which extend in the direction into and out of the page. Without wishing to be bound by theory, it is believed that such corrugations or rugosities enhance the scrubbing and dispersing performance of the front outer surface and may provide built-in void space for trapping dust, dirt, and particulate material. The texture of the extensible film also provides a better aesthetic feel to the hand and provides an elastic fit desired in a glove or mitt.

FIG. 12 is a perspective view of one suitable material and structural configuration for a barrier layer 25 in accordance with FIG. 11, such material being consistent with the materials disclosed and claimed in the aforementioned commonly-assigned U.S. patents to Chappell, et al., and Anderson, et al. Such materials typically provide for extensibility, and (if applicable) elastic recovery, in a predominant direction illustrated via the use of the arrow labeled "D" in FIG. 12. When such a directional material is utilized in the construction of an applicator consistent with FIG. 11, the direction "D" would be oriented perpendicular to the direction in which it is desired for the rugosities to extend. Said differently, for the embodiment of FIG. 1 the direction "D" for the barrier layer 25 is left to right across FIG. 11 while the rugosities 50 extend in the direction into and out of the page.

To facilitate spreading or dispersal of the substance upon the target surface, particularly to counteract the tendency of the substance to remain in a localized distribution pattern given the localized orientation upon the deformable substance, it is presently preferred to utilize substances which are tailored so as to be wettable on the target surface. Other factors which may aid in dispersion or distribution of the substance upon the target surface include the use of substances which exhibit a shear-thinning behavior, as well as mechanical spreading action provided by the user of the composite sheet material to impart a lateral mechanical motion after activation but prior to removal of the deformable material from the target surface. Such lateral mechanical action may also provide additional interaction with the substance such as for shear-thinning substances and may provide additional benefits such as lathering, foam generation, scrubbing/abrasive action, etc.

Successful dispersal occurs when a portion of the deposited or dispensed substance subsequently coats a portion of the target surface where the substance was not originally deposited. Upon removal of the sheet material from the target surface, at least some of the substance remains located on the target surface, preferably in a substantially-uniform fashion.

The mitts of the present invention may be packaged in any suitable fashion. However, a presently preferred method of packaging the mitts involves tri-folding them in a C-folded configuration, then stacking a plurality of folded mitts within an outer carton or wrapper. It is believed that the "cushioning" effect of the superposed folded portions of the mitts provides additional protection against premature rupture of the fluid reservoirs.

Applicators in accordance with the present invention may find utility in many situations. One example of a mitt construction might include a substrate on one side suitable for dusting furniture, etc., and the other side could be a substrate suitable for polishing furniture, etc. This polishing substrate would be either pre-moistened with a lotion or this side could have a burstable pouch that could dose the desired amount of polishing wax as needed.

Another example of an applicator made in accordance with the present invention would include a glass cleaning mitt provided as a flexible structure for distributing glass cleaning substance onto a target glass surface. Such an applicator might preferably include a first fluid-containing reservoir having a predetermined amount (e.g., 6–10 cc's) of a liquid cleaning product such as the CINCH® brand product as available from The Procter & Gamble Company, Cincinnati, Ohio. The mitt itself might preferably include a layer of polypropylene spunbonded nonwoven material for providing a substrate for spreading the cleaning substance and scrubbing such surface with the cleaning solution. For glass cleaning, such a spunbonded nonwoven might be provided of a basis weight from about 17 to 35 gsm in order to provide sufficient durability and strength to provide a robust glass cleaning product. Such spunbonded nonwoven is commercially available such as from BBA Nonwoven of Simpsonville, S.C., under the Celestra name. This material would also preferably be substantially free of surfactants or other treatments which might leave residual material on the surface being cleaned. It might also be preferred to provide the reservoir with a frangible seal connected to a distribution channel providing fluid communication with one or more distribution apertures located in a region or application surface of the mitt corresponding to the position of a user's fingers in use.

The reservoir 30 and distribution channel 44 shown in FIG. 7 might be a suitable arrangement for this glass cleaning mitt example. The reservoir itself would be preferably located on the mitt near a cuff region spaced from the application surface or application region, which might be located near the palm of the user in use. This location would space the reservoir away from the region of the mitt which would typically encounter application and scrubbing forces in use, and would require activation by specifically applying force to the cuff region for selectively dispensing the fluid.

In such a glass cleaning mitt example, the reservoir would be ideally located between a layer of tissue or other wicking material (e.g., 37) and a barrier layer (e.g., 25), where the wicking layer would assist in spreading the fluid throughout the nonwoven surface of the mitt during application. While the barrier layer kept the fluid from contacting the user. On the back side of the mitt, a substantially absorbent material such as the Bounty Rinse and Reuse(& product discussed earlier might preferably be utilized to provide a distinct surface for removing and absorbing residual glass cleaning product and dirt left on the glass after cleaning with the nonwoven side of the mitt.

In another example, the glass cleaning formula preferably leaves a hazy film when applied to the surface, and the back side absorbent material can then be used to "buff", shine and remove all materials on the glass from the cleaning phase. Formulas that provide the hazy film desired can include a combination of silicone polymers, glycol ethers, and non-scratching abrasives. Upon application of the fluid using the nonwoven side of the mitt, the user would see a hazy film wherever the formula had been applied. The spaced reservoir could be squeezed as appropriate to dose the fluid in appropriate amounts onto the surface to be cleaned, while the barrier layer (e.g., 25) would keep the user's hand isolated from the cleaning formula. Turning the mitt over, the absorbent side could then be used to buff and remove all residuals from the glass surface.

Another example might be a mitt suitable for Pet Care applications. The mitt could have an odor absorbing non-woven structure like an activated carbon cloth that would absorb pet odors and the back side could be a different nonwoven with a bursting pouch containing a conditioner or possibly an odor neutralizing liquid such as FEBREZE®, a product marketed by The Procter & Gamble Company. The mitt would allow the pet owner to rub around the pet's face without worrying about the need to control a spray or stream of liquid product.

Other Examples include mitts for cleaning and conditioning the skin of babies, where one side provides a cleansing function while the other side delivers lotion & fragrance for moisturing baby skin and preventing diaper rash.

Applicators with or without a bursting pouch can be designed to accomplish any of the following:

Cleaning a surface (scrubbing, applying a cleaner, etc . . . )

Absorbing or picking up from a surface (dirt, moisture, dry particles, dust, pet hair, grime, grease, body waste (baby diaper changing)).

Rinsing a surface (water or neutralizing substance)

Applying a substance (lotion, treatment, cream, polishing substance, etc.)

Figure 15:
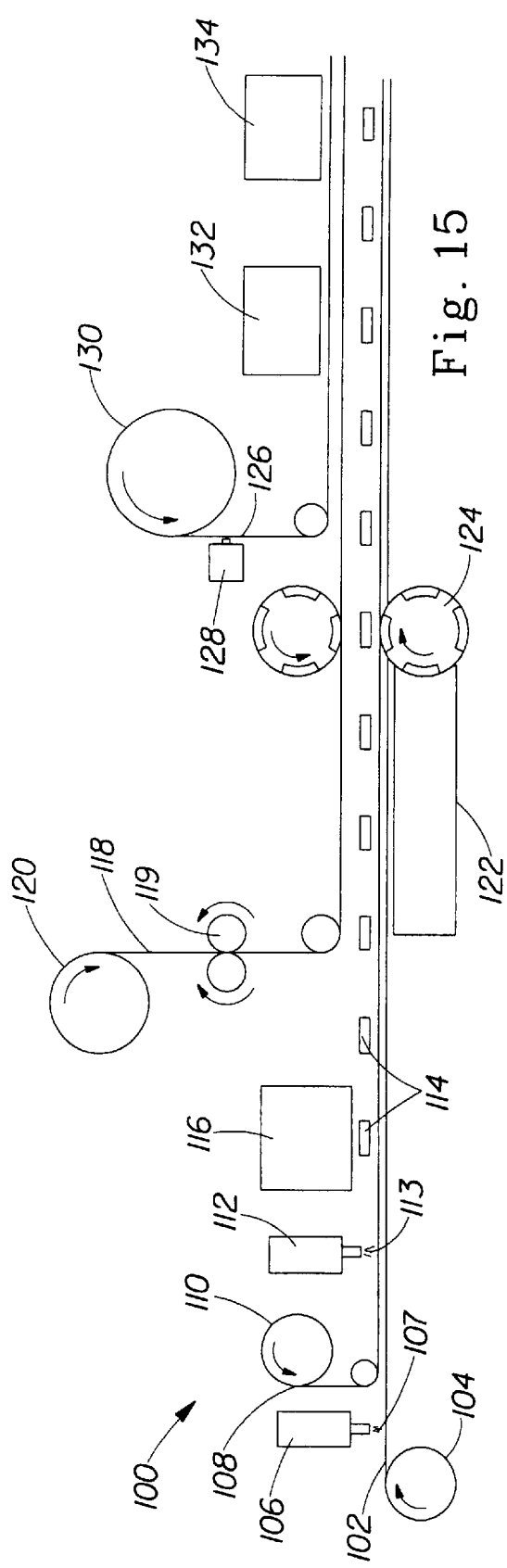
FIG. 15 is a schematic illustration of an applicator manufacturing process in accordance with the present invention.
Figure 16:
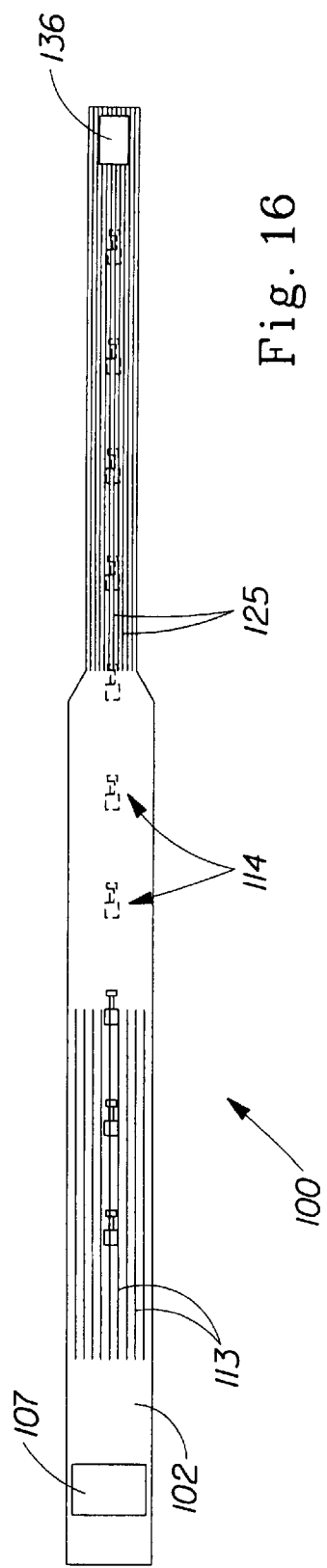
FIG. 16 is a plan view of the process of FIG. 13.

Manufacturing Process:

A manufacturing process suitable for manufacturing applicators in accordance with the present invention is schematically illustrated in FIGS. 15 and 16.

As shown in FIG. 15, the process 100 begins with the feeding of a first web 102 from a supply roll 104. The first web 102 corresponds to the front panel 24 of FIG. 2. A glue applicator 106 applies a thin layer of adhesive 107 to the upper surface of the first web 102 in a suitable pattern for substantially uniform coverage, such as a spiral pattern as shown more clearly in FIG. 16. The adhesive is used to establish a bond between the first web 102 and the second web 108, which is fed from a supply roll 110, to form a composite web. The second web 108 corresponds to the tissue layer 37 shown in FIG. 2.

Once the first and second webs are secured to form a composite web, at least one reservoir 114 (corresponding to the reservoir 30 of FIG. 2) is placed in an appropriate location in relation to the web dimensions so as to be located within the dimensions of the finished applicator. Any suitable apparatus 116, such as a "pick and place" apparatus, may be utilized to place the reservoirs 114 upon the traveling composite web. Beads of adhesive 113 from an adhesive applicator 112 may be utilized to secure the reservoirs 114 in place.

Next, the third web 118 corresponding to the barrier layer 25 of FIG. 2 is applied, first being fed from a supply roll 120 through a pair of opposing rolls 119 which perform the "elasticizing" operation to selectively strain the web to impart elastic-like properties, as described above. The web 118 is then applied to the composite web over the reservoirs 114, and is held in a tensioned condition via the use of any suitable apparatus 122, such as a "vacuum conveyor". The web is preferably stretched by at least 30%, and preferably at least 50%, when it is attached to at least one other web to obtain the desired level of rugosities. The composite web then passes through a sealing/bonding apparatus 124, such as a pair of compression rolls (with cavities as necessary to avoid prematurely rupturing the reservoir 114), which bonds the composite web together with the barrier layer in the stretched condition. As best seen in FIG. 16, the cross-direction tension on the composite web is then released and the contraction of the third web causes the first and second webs to corrugate or pleat to form the plurality of rugosities 125, corresponding to the rugosities 50 of FIG. 11.

Finally, the fourth web 126 corresponding to the back panel 26 of FIG. 2 is unwound from supply roll 130, optionally coated with a friction-enhancing substance from applicator 128, and then applied to the composite web. As mentioned earlier, friction-enhancing elements can be added in various forms such as panels, strips and beads, in addition to coatings. Consequently, such elements could alternatively be added to one or more of the webs joined to define the internal cavity as described, such as by adhesive, spray coating, heat sealing or other lamination techniques as known in the industry. A suitable apparatus 132 such as a continuous rotary heat sealing apparatus then joins the fourth web to the remainder of the composite web by forming a peripheral heat seal around the edge of what will become the finished applicator, such as a mitt, in the desired outline shape. A rotary die cutting apparatus 134 then severs the finished applicator from the excess material of the rest of the web to form finished applicator or mitt 136. Finished applicators may then be folded, if desired, via the use of folding boards or other suitable apparatus (not shown) and packaged as desired.

Processing conditions for the above process may be determined in accordance with procedures known in the art for establishing suitable operating conditions such as seal temperatures, nip pressures, line speeds, and the like.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

Figure 14:
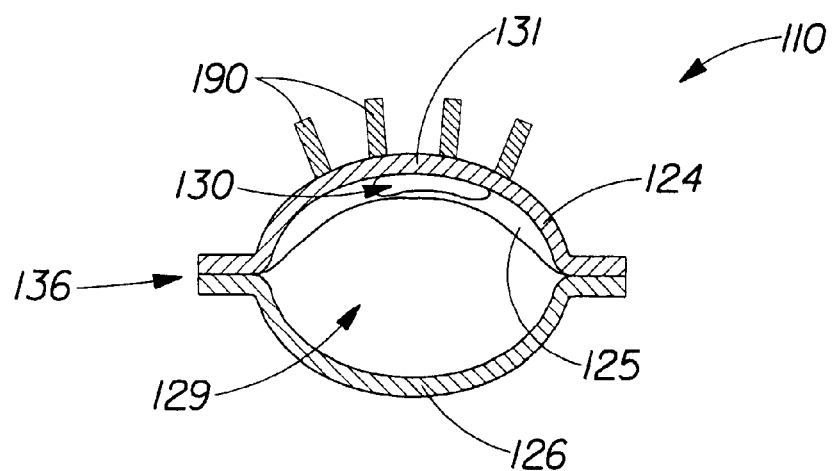
FIG. 14 is a cross-sectional view of the finger mitt applicator of FIG. 13, taken along line 14—14.

For example, a mitt that fits on at least a part of one or more fingers only may be preferable for getting into tight spots or for better dosing control and dispensing accuracy. Applications for these finger or digit mitts would include applicators for facial creams, anti-wrinkling creams, cosmetics, liquid foundation, toothpaste, sunscreen, and others. The finger mitt would have a similar construction as the hand mitts, but would be sized to only fit part of one or more fingers. FIGS. 13 and 14 show such a finger mitt 210 for dispensing toothpaste on the edge of the finger as needed. A cylindrical hollow interior 229 into which at least a portion of a user's digit could be inserted as illustrated, having a front panel 224 with optional outwardly extending bristles 190 on front outer surface 231 for a toothbrush or a scrubbing application. A reservoir 230 similar to that shown and discussed herein with respect to FIGS. 3 and 7 is shown in phantom. This same mitt could also be used to dispense a variety of other lotions, creams, or liquids to a specific location.

Another example would be a facial lotion that could be applied close to the eyes with a finger applicator. This applicator would allow the consumer to very precisely control where the product was applied without fear of getting in the eye. A suitable soft substrate, such as an open or closed cell polyethylene foam, could be used as the applicator substrate or front panel 224 to provide a very soft and smooth application surface for applying the product. Bristles (e.g., 190) or abrasive coatings can be applied to either substrate to provide additional scrubbing or cleaning capability. One way to apply bristle-like fibers to the substrate would be to use a hot melt screen printing process as known in the art, or the adhesive pattern printed is elongated in a direction generally perpendicular to the substrate cleaning bristles extending upwardly from the substrate.

These smaller mitts would preferably be formed of a substrate such as front panel 224 for applying the product, a rupturable reservoir 230 barrier layer 225 to keep product from contacting the skin, and a second substrate to create the internal cavity for the finger. The second substrate can also be designed to absorb liquid in the same way as the larger mitts for the hands. Of course, mitts could also be designed to go onto the foot, toes, or a reusable molded applicator part (not shown) meant to be used as an application device. The barrier layer and/or the substrates can also be made at least partially extensible, and can include a friction enhancing element, as described herein, to better fit and stay on the finger. Other alternatives and modifications will be apparent to those skilled in the art without departing from the scope of the present invention.

What is claimed is:

1. A semi-enclosed applicator for distributing a product onto a target surface, said applicator having a first absorbent and outwardly facing side, a second non-absorbent and outwardly facing side opposed to said first side, and an internal cavity between said first and second sides, said applicator further having at least one opening such that said internal cavity is externally accessible, said applicator comprising:

(a) at least one substantially fluid-impervious barrier layer within said internal cavity adjacent at least one of said sides;

(b) a first rupturable, product-containing, laminate flexible film reservoir, said reservoir having at least one weak region located adjacent one of said sides; and wherein said product is released to said target surface through said weak region upon application of pressure to said rupturable reservoir.

2. The applicator of claim 1, wherein at least a portion of one of said first and second sides is differentially extensible.

3. The applicator of claim 1, further comprising a fluid pathway through which product is dispensed from said rupturable reservoir, said fluid pathway being normally closed except when product dispensing is desired.

4. The applicator of claim 1, wherein said second side comprises a first material selected to facilitate dispensing and application of said product from said rupturable reservoir, and said first side comprises a second material at least partially absorbent of said product from said rupturable reservoir to facilitate removal thereof from a surface.

5. The applicator of claim 1, wherein said first rupturable reservoir is provided with a frangible seal having a resistance to bursting.

6. The applicator of claim 5, further comprising at least one foldable portion located adjacent said frangible seal, and wherein said applicator has a folded condition in which said foldable portion is folded and the resistance to bursting forces of said frangible seal is significantly increased.

7. The applicator of claim 1, further comprising structure to temporarily increase the resistance to bursting of said rupturable reservoir.

8. The applicator of claim 1, further comprising two dispensing apertures in fluid communication with said rupturable reservoir, said two dispensing apertures being oriented away from each other.

9. The applicator of claim 1, further comprising a second product-containing reservoir in selective fluid communication with one of said first side, second side, first inside surface, and second inside surface.

10. The applicator of claim 9, wherein said first and second reservoirs are each configured to be rupturable at predetermined pressures, such that the first and second reservoirs can be selectively activated in predetermined sequence to allow at least one of simultaneous distribution, product dosing, mixing and sequential distribution of the respective products as needed.

11. The applicator of claim 1, further comprising a friction enhancing element located at least partially within said internal cavity during use.

12. The applicator of claim 1, further comprising a layer of wicking material located adjacent said second side, said wicking material including wicking properties with respect to the product in said first rupturable reservoir.

13. The applicator of claim 1, wherein said applicator is provided in the form of a mitt to be used on at least a portion of the hand of a user.

14. The applicator of claim 1, further comprising a barrier layer which is substantially impervious to said product, said barrier layer being located at least partially between said first side and said internal cavity.

15. The applicator of claim 14, wherein said product comprises a glass cleaning formula, and said applicator is provided in the form of a mitt, said internal cavity being sized and configured to receive the hand of a user.

16. A method for forming the semi-enclosed applicator of claim 1, said method comprising the steps of:

providing a first web corresponding to one of the first and second sides;

providing a second web corresponding to the other of said first and second sides;

placing a first product-containing flexible film reservoir having at least one weak region in a predetermined location in relation to said first web and said second web;

securing said reservoir relative to said first web and said second web and attaching said first web and said second web to one another in such a way as to form an externally accessible internal cavity therebetween; and, cutting the applicator in a desired outline shape from the balance of the respective webs to define the finished applicator.

17. The method of claim 16, further comprising the step of providing a third web of at least partially extensible material and attaching the third web to at least one of said first and second webs in a tensioned condition.

18. The method of claim 17, wherein at least a portion of said third web is stretched at least 30% when it is attached to the at least one other web.

19. The applicator of claim 1, further comprising a plurality of distribution apertures through which product may be dispensed from said first rupturable reservoir, said reservoir being disposed adjacent one of said sides.

20. The applicator of claim 1, further comprising at least two distribution apertures in communication with said rupturable reservoir, said at least two distribution apertures being oriented away from each other.

21. A semi-enclosed applicator for distributing a product onto a target surface, said applicator having a first absorbent and outwardly facing side, a second non-absorbent and outwardly facing side opposed to said first side, and an internal cavity between said first and second sides, said applicator further having at least one opening such that said internal cavity is externally accessible, said applicator comprising:

(a) at least one substantially fluid-impervious barrier layer within said internal cavity adjacent at least one of said sides;

(b) a rupturable product-containing reservoir, said rupturable reservoir having at least one weak region having a comparatively low burst force, located adjacent one of said sides; and, wherein said rupturable reservoir is adapted to release said product upon application of pressure to said rupturable reservoir.

22. The applicator of claim 21, wherein at least a portion of one of said first and second sides is differentially extensible.

23. The applicator of claim 21, further comprising a friction enhancing element located at least partially within said internal cavity during use.

24. The applicator of claim 21, wherein said first side comprises a first material at least partially absorbent of said product from said rupturable reservoir to facilitate removal thereof from a surface, and said second side comprises a second material selected to facilitate dispensing an application of said product from said rupturable reservoir.

25. The applicator of claim 21, wherein said first rupturable reservoir is provided with a frangible seal having a resistance to bursting.

26. The applicator of claim 25, further comprising at least one foldable portion located adjacent said frangible seal, and wherein said applicator has a folded condition in which said foldable portion is folded and the resistance to bursting forces of said frangible seal is significantly increased.

27. The applicator of claim 21, further comprising structure to temporarily increase the resistance to bursting of said rupturable reservoir.

28. The applicator of claim 21, further comprising a dispensing aperture spaced from said rupturable reservoir.

29. The applicator of claim 21, wherein said applicator is provided in the form of a mitt to be used on at least a portion of the hand of a user.

30. A semi-enclosed applicator for distributing a product onto a target surface, said applicator having a first absorbent and outwardly facing side, a second non-absorbent and outwardly facing side opposed to said first side, and an internal cavity between said first and second sides, said applicator further having at least one opening such that said internal cavity is externally accessible, said applicator comprising:
(a) at least one substantially fluid-impervious barrier layer within said internal cavity adjacent at least one of said sides;
(b) a product-containing flexible film reservoir located adjacent one of said sides, said reservoir being formed with at least one permanent seal and at least one frangible seal; and,
wherein said product is released from said reservoir to said target surface through said at least one frangible seal upon the application of pressure to said rupturable reservoir wherein said pressure ruptures said at least one frangible seal.

31. The applicator of claim 30, wherein at least a portion of one of said first and second sides is differentially extensible.

32. The applicator of claim 30, further comprising a fluid pathway through which product is dispensed from said rupturable product-containing reservoir, said fluid pathway being normally closed except when fluid dispensing is desired.

33. The applicator of claim 30, wherein said first side comprises a first material at least partially absorbent of said product from said rupturable reservoir to facilitate removal thereof from a surface, and said second side comprises a second material selected to facilitate dispensing an application of said product from said rupturable reservoir.

34. The applicator of claim 30, further comprising at least one foldable portion located adjacent said at least one frangible seal, and wherein said applicator has a folded condition in which said foldable portion is folded and the resistance to bursting forces of said frangible seal is significantly increased.

35. The applicator of claim 30, further comprising structure to temporarily increase the resistance to bursting of said rupturable reservoir.

36. The applicator of claim 30, further comprising a dispensing aperture spaced from said rupturable reservoir.

37. The applicator of claim 30, further comprising a friction enhancing element located at least partially within said internal cavity during use.

38. The applicator of claim 30, further comprising a layer of wicking material located adjacent at least one of said first and second sides, said wicking material including wicking properties with respect to the product in said rupturable reservoir.

39. The applicator of claim 30, wherein said applicator is provided in the form of a mitt to be used on at least a portion of the hand of a user.

* * * * *